United States Patent [19] [11] 4,020,268
Nishikawa et al. [45] Apr. 26, 1977

[54] AGAROSE CONTAINING AFFINITY MATRIX MATERIALS

[75] Inventors: A. Hirotoshi Nishikawa; Harry F. Hixson, Jr., both of Webster, N.Y.

[73] Assignee: Xerox Corporation, Stamford, Conn.

[22] Filed: Nov. 21, 1974

[21] Appl. No.: 526,028

Related U.S. Application Data

[62] Division of Ser. No. 306,241, Nov. 13, 1972, abandoned, which is a division of Ser. No. 141,778, May 12, 1971, Pat. No. 3,746,622.

[52] U.S. Cl. .................................... 536/1; 195/63; 195/66 R; 260/112 R; 260/112.5 R; 536/2; 536/43; 536/51; 536/56; 536/62; 536/90; 536/112

[51] Int. Cl.² ................. C07H 11/02; C08B 37/02; C08B 37/06

[58] Field of Search ................... 260/209 R; 536/1

[56] References Cited

UNITED STATES PATENTS

| | | | |
|---|---|---|---|
| 3,507,851 | 4/1970 | Ghetie et al. | 260/209 R |
| 3,651,043 | 3/1972 | Schell et al. | 260/209 R |
| 3,810,882 | 5/1974 | Browning et al. | 260/209 R |

Primary Examiner—Johnnie R. Brown

[57] ABSTRACT

A novel affinity matrix material for trypsin and trypsin-like enzymes is disclosed. Methods employing this material to isolate and/or purify crude extracts containing trypsin and trypsin-like enzymes and to store the purified enzymes obtained are also disclosed.

1 Claim, No Drawings

AGAROSE CONTAINING AFFINITY MATRIX MATERIALS

This is a division of application Ser. No. 306,241 filed Nov. 13, 1972, and now abandoned, which was a division of application Ser. No. 141,778 filed May 12, 1971, and now U.S. Pat. No. 3,746,622.

BACKGROUND OF THE INVENTION

This invention relates generally to enzyme purification and/or isolation by employing the substrate specificity of an enzyme, and more specifically to the purification and/or isolation from complex mixtures of materials of trypsin and trypsin-like proteolytic enzymes which include: trypsin (E.C.3.4.4.4), carboxypeptidase B (E.C.3.4.2.2), papain (E.C.3.4.4.10), ficin (E.C.3.4.4.12), thrombin (E.C.3,4,4,13), plasmin (E.C.3.4.4.14), subtilopeptidase A(E.C.3.4.4.16), aspergillopeptidase A(E.C.3.4.4.17), streptococcus peptidase A(E.C.3.4.4.18), clostridiopeptidase B(E.C.3.4.4.20), bromelain (E.C.3.4.4.24), and urokinase (E.C.3.4.4.a). A trypsin-like enzyme is hereby defined as a hydrolytic enzyme belonging to the Enzyme Commission (E.C.) class 3.4.-.-. and having a specificity for peptide bonds as well as ester bonds on arginine and lysine residues (Report of the Commission on Enzymes of the International Union of Biochemistry, Pergamon Press, Oxford, (1961)).

Generally known procedures for enzyme isolation employed in the prior art involve an array of discrete techniques which are used in empirically determined combinations. These techniques depend for the most part on some gross molecular parameter of the enzyme of interest such as its solubility in salt solutions, for example, in ammonium sulfate solutions or water miscible organic solvents, for example, ethanol, or acetone, or its electrical properties, as used in electrophoretic processes, isoelectric precipitation or ion exchange chromatography. In addition, molecular size has been used to purify enzymes as in dialysis, in gel filtration chromatography, and in ultrafiltration. Selection of any of these methods, singularly or in combination, is made in the prior art to optimize purification and recovery of the enzyme. Trypsin has been purified from bovine pancreas, employing methods more specifically outlined in an article by M. Laskowski in *Methods In Enzymology*, Vol. II, page 26, 1955. In this method minced pancreas is extracted with dilute sulfuric acid and treated with ammonium sulfate in several discrete steps to remove ribonuclease and alpha-chymotrypsinogen. The pH of the resulting solution is adjusted to 3.0 and treated with ammonium sulfate to precipitate the trypsinogen. This material is then extracted with 0.4 saturated ammonium sulfate solution and reprecipitated with additional ammonium sulfate. After washing with an acidified magnesium sulfate solution, the crude trypsinogen is dissolved in a pH 8 buffer containing $CaCl_2$ and stored for 24 hours at 4° C. The trypsin so obtained is then purified by further ammonium sulfate precipitations and extractions. This procedure is an example of purifying trypsin by solution-property methods.

Another method employed in the prior art is reported by Feinstein (FEBS Letters, 7: 353 [1970]). In this method trypsin is purified by adsorption onto an agarose column which contains covalently bound ovomucoid, a trypsin inhibiting protein obtained from chicken egg. The catalytically active trypsin is separated from non-active trypsin as well as from alpha-chymotrypsin. This technique is also referred to as enzyme-specific chromatography by Baker (Design of Active-Site-Directed Irreversible Enzyme Inhibitors, Wiley, N. Y. 1967) as well as affinity chromatography by Cuatrecasas, et al. (Proc. Natl. Acad. Sci., U.S., 61:636 [1968]). These methods differ from previously established enzyme purification methods in that the biocatalytic specificity of the enzyme is the means employed to achieve the purification.

Small molecule inhibitors in addition to the macromolecular inhibitors of trypsin and trypsin-like enzymes have been taught (Vogel, et al., Natural Proteinase Inhibitors, Academic, N. Y., 1968). Alkyl and aryl guanidines and amidines are known to be inhibitors of this type (Mares-Guia and Shaw, J. Biol. Chem. 240: 1579 (1965)).

Although the solution-property techniques have been employed and are currently employed to purify trypsin and trypsin-like enzymes among others, they have been proven to be inefficient in operation, expensive and time consuming. While the affinity method of Feinstein represents a simplification over solution-property techniques of enzyme purification, the use of macromolecular proteinase inhibitors has the following deficiencies. The macromolecular inhibitors have a broad enzyme specificity, furthermore these inhibitors must carefully be purified before they can be used in affinity matrices. Also, the concentration of these inhibitors in the affinity matrix is not easily controlled. Hence, there has been demonstrated a continuing need to provide simpler materials and more efficient methods to obtain these enzymes in higher yield and higher purity than heretofore possible.

SUMMARY OF THE INVENTION

It is, therefore, an object of this invention to provide a system devoid of the above-noted deficiencies.

Another object of this invention is to provide a system for purifying trypsin and related enzymes by the use of novel affinity matrices.

Still another object of this invention is to provide a system for purifying trypsin and trypsin-like enzymes employing affinity adsorbents which contain low molecular weight ligands thereby providing higher specificity and ease of incorporation and concentration control of the ligand in the matrix.

Still another object of this invention is to provide a system which employs novel affinity adsorbents as storage materials for purified enzymes.

Yet another object of this invention is to provide novel affinity adsorbent materials.

These and other objects are accomplished in accordance with the system of the present invention by providing an insoluble affinity matrix or carrier material which is capable of biospecifically binding trypsin and trypsin-like enzymes. This affinity matrix contains chemical compounds hereinafter called ligands which have affinity for the desired enzymes and satisfy the following structure:

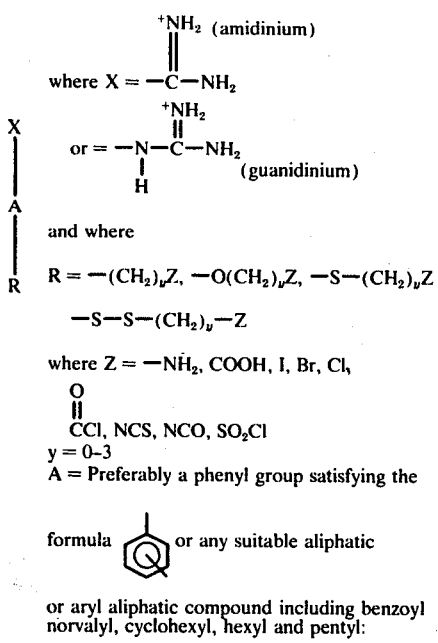

where $X = -\overset{\overset{+NH_2}{\|}}{C}-NH_2$ (amidinium)

or $= -\overset{}{\underset{H}{N}}-\overset{\overset{+NH_2}{\|}}{C}-NH_2$ (guanidinium)

and where $R = -(CH_2)_yZ$, $-O(CH_2)_yZ$, $-S-(CH_2)_yZ$ $-S-S-(CH_2)_y-Z$ where $Z = -NH_2$, COOH, I, Br, Cl, $\overset{O}{\underset{}{\|}}$
CCl, NCS, NCO, SO$_2$Cl y = 0-3

A = Preferably a phenyl group satisfying the formula ⌬ or any suitable aliphatic or aryl aliphatic compound including benzoyl norvalyl, cyclohexyl, hexyl and pentyl:

The ligand molecules are covalently attached to the insoluble carrier or matrix via a linear molecule hereinafter called a leash.

The affinity matrix so produced is then employed in a column into which is introduced a crude extract of material containing trypsin or trypsin-like enzymes from a biological source which has been previously treated to remove insoluble material and to obtain the proper pH and salt concentration. The extract is allowed to percolate through the column in order to cause the trypsin to trypsin-like enzymes to biospecifically adsorb into the affinity matrix and allow all other proteins and biopolymers in the extract which have no specific affinity for the ligand to pass directly through the column. In some cases it is found that a component may be slightly retarded on the column for various non-specific reasons, so that it is desirable to thoroughly wash the column with buffer to completely eliminate all of these non-affinity binding substances. After the column is cleared of these components the specifically adsorbed trypsin or trypsin-like enzyme can be desorbed from the column by percolating through it a solution containing a soluble competitive inhibitor compound which will interact specifically with the adsorbed enzyme. Inhibitors are materials which have analogous functionality to the ligand materials but differ structurally among other things in that they have no analogous leash and matrix material to which they are connected. When isolating some trypsin-like enzymes it has been found useful to desorb them from the column by percolation with buffers of acidic pH. When necessary, a gel filtration column is connected in series with the affinity column after the extraneous components have passed through, thus providing for the efficient removal of the soluble competitive inhibitor compound from the purified enzyme.

These affinity materials also provide a system with which purified trypsin and trypsin-like enzymes may be stored without undergoing degradation of their catalytic activity. This is accomplished by adsorbing these enzymes to the affinity materials and then storing in the cold. Once the enzymes are adsorbed to these materials they are unable to undergo autodegradation, thus eliminating one of the substantial causes of enzyme degradation.

The affinity matrices which comprise this invention may be used in clinical and/or veterinary theraputic procedures, e.g. (1) in an in vivo binding agent or trapping device for trypsin or trypsin-like enzymes; (2) an in vivo agent or device for the administration of trypsin or trypsin-like enzymes for therapeutic purposes; (3) an extracorporeal device such as in a vascular shunt system for removing trypsin or trypsin-like enzymes from the blood; and (4) an injection or similar administrative device for introducing into the patient trypsin or trypsin-like enzymes for therapeutic purposes.

Any suitable matrix material may be employed in the system of the present invention. Typical matrix or carrier materials include: cellulose and all of its refined forms; aminoethyl cellulose; phospho cellulose; diethylaminoethyl cellulose; carboxymethyl cellulose; ECTEOLA cellulose; p-aminobenzyl cellulose; polyethyleneimino cellulose; triethylamino cellulose; sulfoethyl cellulose; guanidoethyl cellulose; agaroses such as, e.g. Sepharose or Bio-Gel A; crosslinked dextrans such as, e.g. Sephadex; crosslinked polyacrylamides such as, e.g. Bio-Gel P agaropectin; and crosslinked or non-crosslinked collagen. These materials are characteristically insoluble in aqueous solutions and preferably have low hydrophobicity and a non-ionic character. A matrix material having an ionic character or having high hydrophobicity may prove to be an impediment in the affinity process.

Coupling reactions suitable for attaching leash and-/or ligand molecules to the matrix or ligand molecules to leash compounds are generally limited by the solvent medium in which they can be carried out. The choice of the solvent medium is predicated by the requirements of the carrier material. Polysaccharide and polyacrylamide carriers are usually employed in water. When necessary, water-miscible organic solvents in appropriate ratios with water can be used, e.g. agarose gels may be mixed with either 50% ethylene glycol or 50% dimethyl formamide (Cuatrecasas, J. Biol. Chem. 245 3059 (1970)).

Although any suitable reaction temperature may be employed preferably from 1° to 30° C is conveniently employed in an aqueous buffer solution of appropriate pH which may or may not include water miscible solvents. The present invention may be practiced by using any suitable coupling reaction. Typical such coupling reaction includes the coupling of carboxylic groups with amino groups or alcoholic groups which may be accomplished, e.g. by the addition of carbodiimides (water-soluble type preferred), or via acyl azides, acyl halides, and acyl anhydrides by the addition of appropriate reagents. A ligand (or leash) containing an amino group may be coupled to a leash (or ligand) containing, e.g. isocyanate, isothiocyanate, sulfonyl chloride, alkyl halide, and methyl or ethyl amidate.

Although any suitable leash molecule may be employed in the system of the present invention, it is preferable that these molecules be linear and hydrophilic, as well as free of strong ionic groups. Typical leash molecules include: epsilon-aminocaproic acid; beta-alanine; 1,6-diaminohexane; bis(3-aminopropyl)amine; glycine; glycylglycine; glycylglycylglycine; succinamidoethylamine; succinamidobutylamine; succinamidohexamethylamine; aminoethanol; 2,2'-diaminodiethyl ether and its higher homologs. The molecular length of the leash compound employed should be long enough to provide the proper relationship of ligand to matrix material so that effective binding of the desired enzyme may be accomplished. In some cases it is found that no leash is required, however, in most cases the leash compound employed is preferably about 7 angstroms or longer.

To further define the specifics of the present invention the following examples are intended to illustrate and not limit the particulars of the present system. Parts and percentages are by weight unless otherwise indicated. All solutions are in water unless otherwise indicated.

EXAMPLE I

To a suspension of agarose gel is added cyanogen bromide at 100 mg/ml of the gel and then titrated to a pH of 11.0 with 4 M sodium hydroxide (NaOH). After alkali uptake ceases, the 'activated' gel is collected on a sintered glass funnel and washed with cold borate buffer having a concentration of 0.1M and a pH of 9.5. Then the gel is resuspended in cold borate buffer and mixed in equal volumes with a solution of 1,6-diaminohexane at 100 mg/ml of gel and the pH is adjusted to 9.5. The mixture so obtained is gently stirred overnite at 4° C. The gel is then washed by pouring into a coarse sintered glass funnel and slowly percolating distilled water through it. The aminohexamethylene-agarose obtained is suspended in an equal volume of distilled water into which is mixed 0.2 gm of succinic anhydride/ml of gel. The pH is adjusted to 6.0 and held there by addition of 4 M NaOH. When base uptake ceases, the mixture is stirred gently for 3 hours at 4° C and then allowed to stand at that temperature overnight. The succinamidohexamethyl-agarose, hereinafter referred to as SHA so obtained is washed on a coarse sintered glass funnel as previously described.

The ligand p-aminobenzamidine monohydrochloride in the amount of 37 mg/ml gel is coupled to the succinyl groups in the SHA gel by reaction in a 0.1M water-soluble carbodiimide solution employing those techniques more fully described by Hoare and Koshland, (J. Biol. Chem. 242: 2447(1967)). The water soluble carbodiimide employed is 1-ethyl-3-(3'-dimethylamino-propyl)carbodiimide monohydrochloride (EDC). The coupling reaction is carried out in an automatic pH-stat at pH 4.75 using 1.0 molar hydrochloric acid, HCl. When proton uptake is observed to cease, the gel slurry is washed on a sintered glass funnel using distilled water applied at 5 times the volume of the gel as previously described. The affinity matrix material obtained is hereinafter referred to as pBz-SHA gel having a ligand capacity of 0.021 meq/ml of gel.

EXAMPLE II

The procedure as outlined in Example I is repeated except that 45 mg/ml of gel of m-aminobenzamidine dihydrochloride is employed as the ligand. The preparation so obtained is hereinafter referred to as mBz-SHA gel having a ligand capacity of 0.012 meq/ml of gel.

EXAMPLE III

The procedure as outlined in Example I is again repeated except that 36 mg/ml of gel of p-aminophenyl-guanidine monohydrochloride is employed as the ligand. The product so obtained is hereinafter referred to as pAG-SHA gel having a ligand capacity of 0.035 meq/ml of gel.

EXAMPLE IV

The procedure as outlined in Example III is again repeated except that epsilon-aminocaproic acid is used instead of 1,6-diaminohexane and the succinylation step is omitted. This preparation is hereinafter referred to as pAG-CA gel.

EXAMPLE V

The procedure of Example IV is repeated except that beta-alanine (3-aminopropionic acid at 44 mg/ml of gel) is employed in place of the epsilon-aminocaproic acid. This preparation is hereinafter referred to as pAG-AA gel and is found to bind trypsin to a lesser extent than the preceeding examples.

EXAMPLE VI

The procedure as outlined in Example II is repeated except that cyanogen bromide is employed at 200 mg/ml of gel and 1,6-diaminohexane is employed at 180 mg/ml of gel. Correspondingly higher concentrations of succinic anhydride are used in the leash succinylation and the mBz coupling reaction using 40 mg/ml gel is conducted employing 0.1 molar EDC. The mBz-SHA gel obtained is found to have a higher concentration of ligand per milliliter of gel (0.06 meq/ml of gel).

EXAMPLE VII

Amino-ethyl cellulose (AE-cel), containing 0.27 meq of amine/gm of dry cellulose, is swollen in 0.1M sodium bicarbonate (NaHCO$_3$), then washed with 0.1M NaOH, then with 0.1M HCl and then distilled water. The suspension of 10 gm AE-cel in 80 ml of water is then treated with 3 gm succinic anhydride at pH 6.0 which is maintained with 4M NaOH while monitoring with a pH meter. When uptake of base ceases, the mixture is stirred at 4° C for 2 hours. After washing the suspension thoroughly with water, it is mixed with 0.93 gm mBz and reacted with 2.3 gm of EDC as described before in Example I. A somewhat flocculent suspension results hereinafter referred to as pAG-SA cel.

EXAMPLE VIII 500 ml of anhydrous ethylenediamine is preheated in a stoppered flask to 90° C and 25 gm of dry BIO-GEL P-300 polyacrylamide beads are added and the slurry is stirred continuously for 8 hours. The flask is then cooled for 1 hour in ice water and then the gel slurry is mixed with 500 ml of crushed ice. The gel is then washed with 0.1M NaCl solution on a Buchner funnel until the washings are free of ethylenediamine as indicated by reaction with 2,4 dinitrofluorobenzene. The gel is then transferred to a large polyethylene beaker and sufficient 0.1M NaCl added to give a thin slurry. The pH of this slurry is adjusted to 6.0 and 25 gm of succinic anhydride is added portionwise while the pH is held at 6.0 by the addition of 2N sodium hydroxide solution. When the pH of the slurry ceases to change the slurry is covered and allowed to set overnight. The slurry is then washed with 10 liters of 0.1M NaCl on a Buchner funnel. 50 ml of the washed beads are then slurried with 50 ml of distilled water, mixed with 10 gm of mBz and reacted with 2 gm of EDC as described in Example I. This preparation is hereinafter referred to as PAE-mBz.

EXAMPLE IX

A standard tris(hydroxymethyl)aminomethane/potassium chloride (0.05M TRIS/0.5M KCL having a pH of 8.0) buffer (hereinafter referred to as TRIS/KCl buffer) is used to equilibrate the affinity column, to dissolve enzyme samples, and to wash the enzyme loaded affinity column. A small chromatographic column tube (0.7 cm × 20 cm) is filled with 7–8 ml of pBz-SHA gel. After equilibration the column is loaded with 40 mg of the purest commercially available trypsin dissolved in about 2 ml of TRIS/KCl buffer. When 0.01 molar benzamidine hydrochloride (Bz) in the TRIS/KCl buffer is percolated through the trypsin-bound column, the trypsin is desorbed by the soluble inhibitor and is specifically washed out in a highly purified state devoid of any degraded trypsin. The column is subsequently eluted with glycine/KCl buffer (0.05M glycine and 0.5M KCl, pH 3.0) resulting in the emergence of little or no protein. The active trypsin so obtained is better than 95% pure as determined by the active-site titration method of Chase and Shaw, Biochem. Biophys. Res. Comm. 29:508 (1967). The yield of 65% obtain herein indicates that the purest commercially available trypsin is only 65% pure. The specificity of the affinity material is verified by loading 40 mg of alpha-chymotrypsin onto a pre-equilibrated column, then washing with the TRIS/KCl buffer containing Bz. Typically, alpha-chymotrypsin is found to pass immediately through the affinity gel. Further, verification of affinity specificity is made by eluting the column with glycine/potassium chloride (0.05M/0.5M pH 3.0) buffer. The column was found to elute protein indicating a properly functioning column.

EXAMPLE X

The procedure as outlined in Example IX is repeated except that in the desorption step 0.001M HCl/0.5M KCl is employed instead of Bz in TRIS/KCl to elute the trypsin from the affinity column. Similar results as obtained in Example IX are observed.

EXAMPLE XI

Bovine thrombin obtained from Parke-Davis Co. is purified on the high capacity mBz-SHA gel as prepared in Example VI according to the procedure in Example IX except that a G-25 Sephadex column 1.5 cm × 30 cm is connected in series to the effluent orifice of the affinity column. The purified thrombin thus obtained is also free of Bz. On a weight basis the thrombin starting material is found to be 1-2% active enzyme.

EXAMPLE XII

The pAG-SHA gel is packed into a 0.7 × 20 cm column (bed volume approximately 8 ml) and is washed with the standard TRIS/KCl buffer. One ml of a trypsin solution (40 mg/ml) is introduced into the column and then washed with the buffer to remove extraneous material. The trypsin adsorbed gel is then stored at approximately 4° C to retard microbial growth on the column.

EXAMPLE XIII

Human urokinase (5000 Ploug units) obtained from Nutritional Biochemicals Corporation is purified on the high capacity mBz-SHA gel as prepared in Example VI according to the procedure as outlined in Example IX except that 0.01M HCl in 0.5M KCl is used to desorb the enzyme from the affinity column. Results similar to those obtained in Example X are observed.

Although the present examples were specific in terms of conditions and materials used, any of the above listed typical materials may be substituted when suitable in the above examples with similar results. In addition to the steps used to carry out the process of the present invention, other steps or modifications may be used if desirable, e.g. ultrafiltration, dialysis or lyophilization may be employed. In addition, other materials may be incorporated in the system of the present invention which will enhance, synergize or otherwise desirably affect the properties of the systems for their use, e.g. water miscible organic solvents may be employed to improve the efficiency of the present system.

Anyone skilled in the art will have other modifications occur to him based on the teachings of the present invention. These modifications are intended to be encompassed within the scope of this invention.

What is claimed is:

1. An affinity matrix material consisting essentially of an insoluble matrix material consisting essentially of agarose covalently bonded to a leash molecule succinaminohexamethylamine which is covalently bonded to a ligand satisfying the formula:

wherein X is

 (amidinium)

or

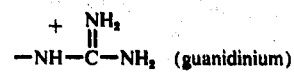 (guanidinium)

A is selected from the group consisting of benzoyl, norvalyl, phenyl, hexyl, cyclohexyl, and pentyl and R is
— $(CH_2)_yZ$,
— $O(CH_2)_yZ$,
— $S(CH_2)_yZ$, or
— $S-S(CH_2)_yZ$
where Z is NH, COOH, I, Br, Cl COCl, NCS, NCO, $SO_2Cl$, and where $y$ is 0 to 3.

* * * * *